United States Patent [19]

Toyoshima

[11] Patent Number: 4,773,105
[45] Date of Patent: Sep. 27, 1988

[54] COLLAPSIBLE SAUNA BOX

[75] Inventor: Takao Toyoshima, Tokyo, Japan

[73] Assignee: Japan Home Sauna Co., Ltd., Tokyo, Japan

[21] Appl. No.: 931,768

[22] Filed: Nov. 17, 1986

[51] Int. Cl.[4] .............................................. A61H 33/06
[52] U.S. Cl. ........................................... 4/526; 4/527; 4/524; 16/291; 219/362; 219/213; 219/385; 200/61.62
[58] Field of Search ................... 4/526, 527, 524, 599, 4/528–532, 600; 16/291–293, 286; 312/258, 259; 248/462; 219/362, 213, 385; 128/371–375; 200/61.82, 61.81, 61.62, 50 A

[56] References Cited

U.S. PATENT DOCUMENTS

| 655,956 | 8/1900 | Cahoon | 4/527 |
| 2,756,299 | 7/1956 | Sunko et al. | 200/61.62 |
| 2,821,982 | 2/1958 | Lyburn | 4/531 |
| 2,891,274 | 6/1959 | Bloom | 16/291 |
| 3,648,299 | 3/1972 | Durst | 4/524 |
| 3,689,718 | 9/1972 | Gorsuch | 200/61.62 |

FOREIGN PATENT DOCUMENTS

| 58-65163 | 4/1983 | Japan . | |
| 89177 | 9/1921 | Switzerland | 128/374 |
| 689294 | 3/1953 | United Kingdom | 4/526 |

Primary Examiner—Henry J. Recla
Assistant Examiner—Linda J. Sholl
Attorney, Agent, or Firm—Jordan and Hamburg

[57] ABSTRACT

A collapsible sauna box is disclosed, which comprises a collapsible box body consisting of front and rear wall members, inwardly foldable left and right side wall members and a ceiling member provided at one end and heaters pivoted for angle adjustment to brackets capable of being mounted inside the collapsible box body at corners thereof. The side wall members, ceiling member and heaters are completely confined between the front and rear wall members overlapped over each other when the collapsible box body is in a collapsed state. In its collapsed state, the collapsible sauna box can be conveniently carried and stored. The heaters are not obstructive in the sauna box in use and can irradiate the user with far-infrared rays in a face-to-face relation to each other on the opposite sides of the user.

8 Claims, 10 Drawing Sheets

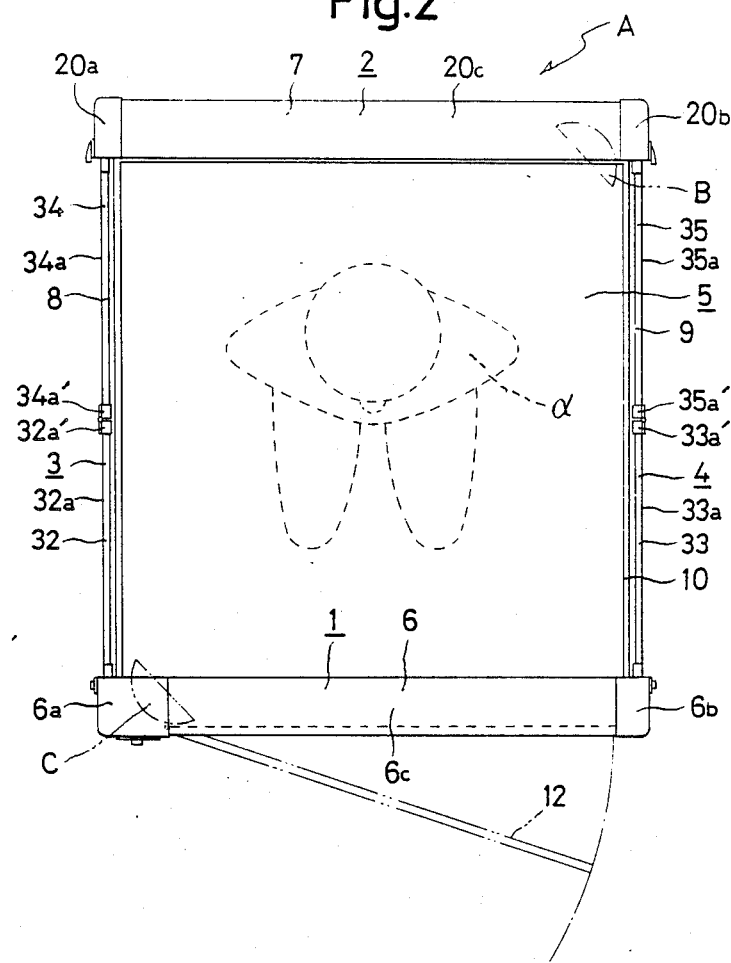
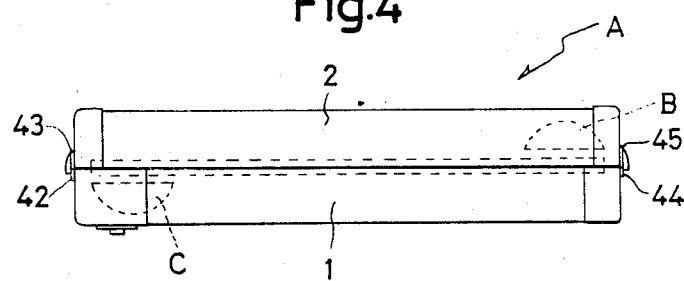

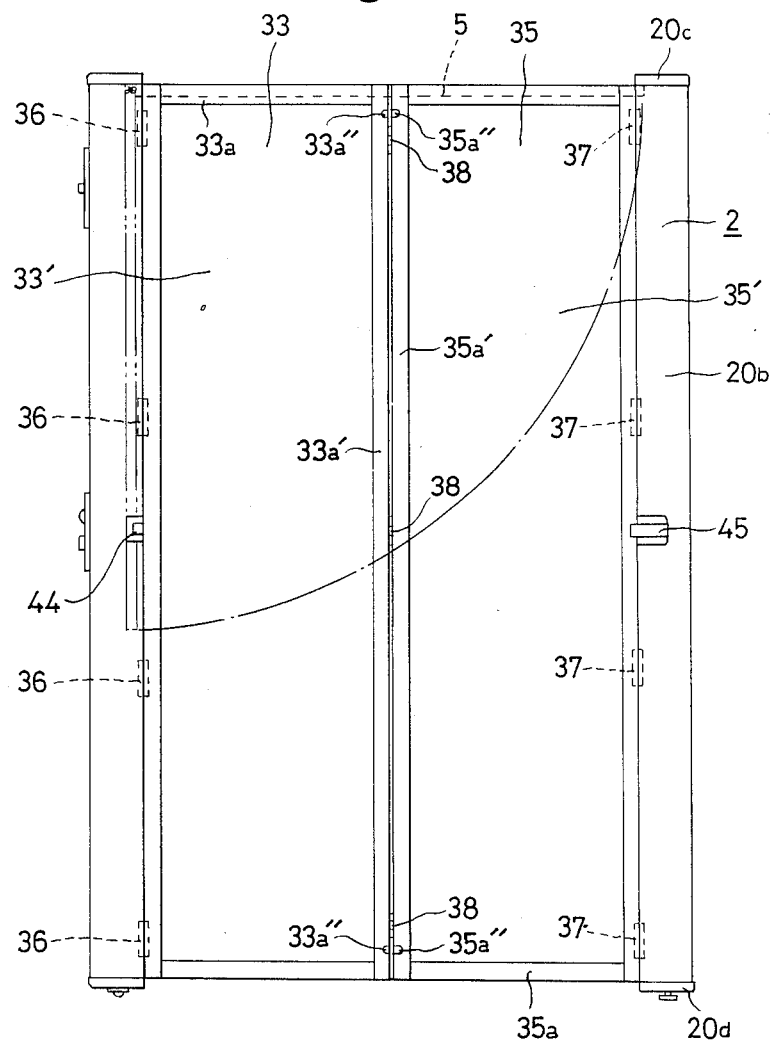

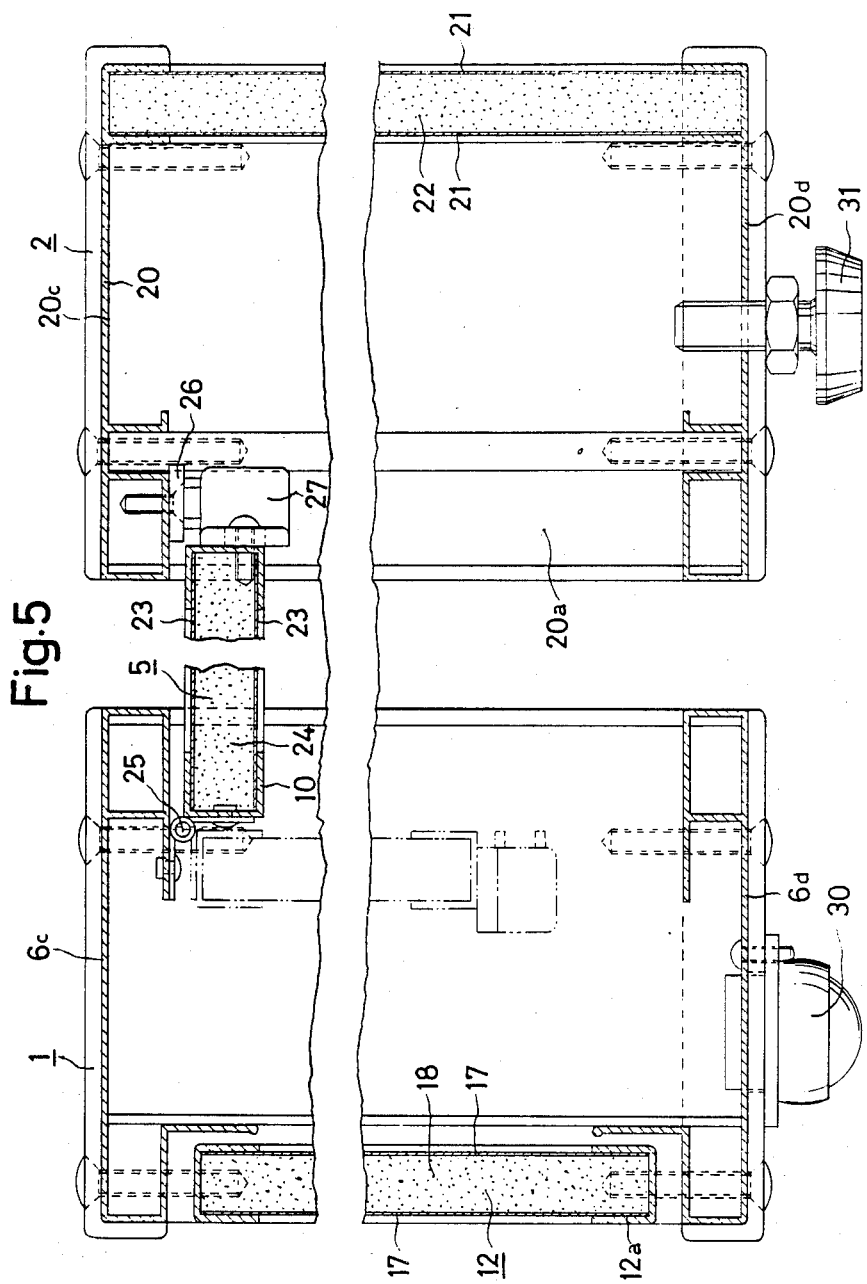

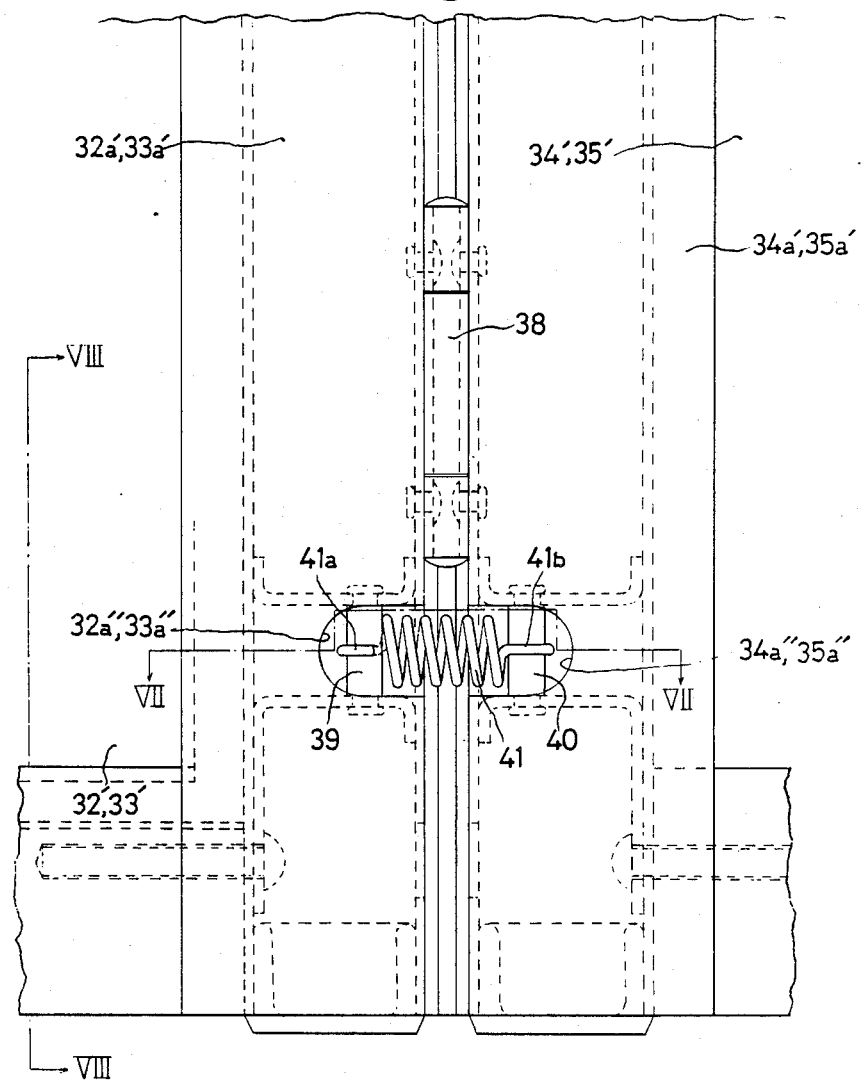

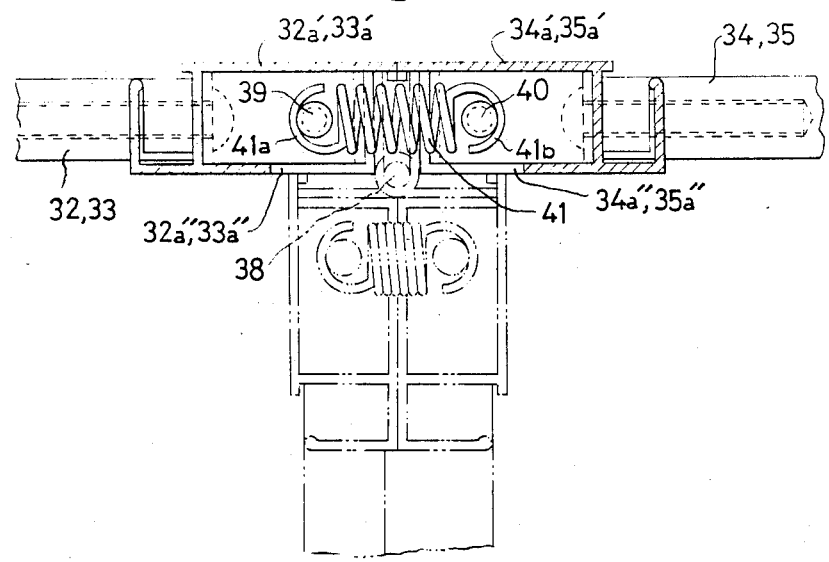
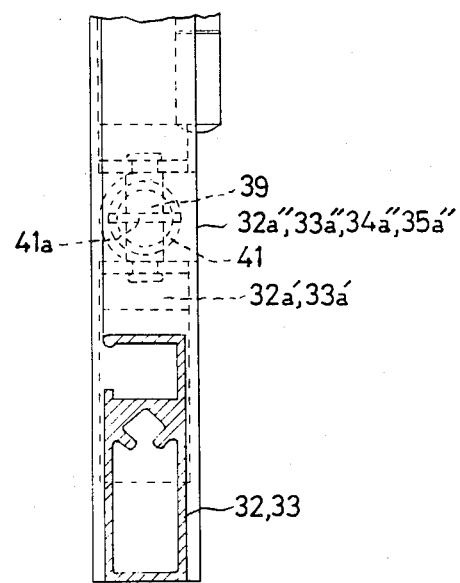

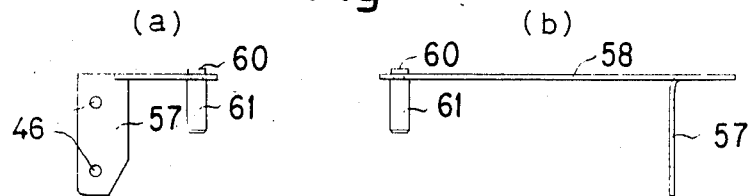
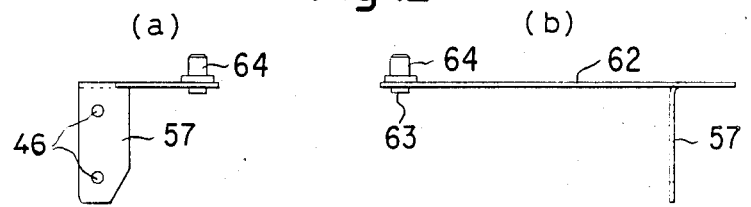
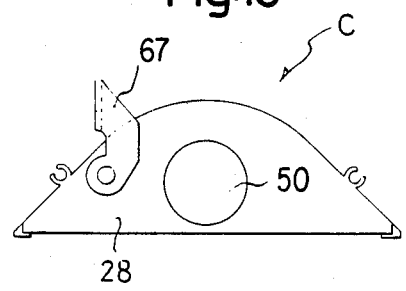
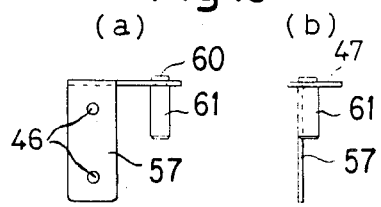
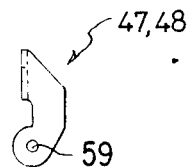
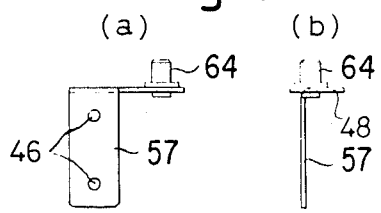

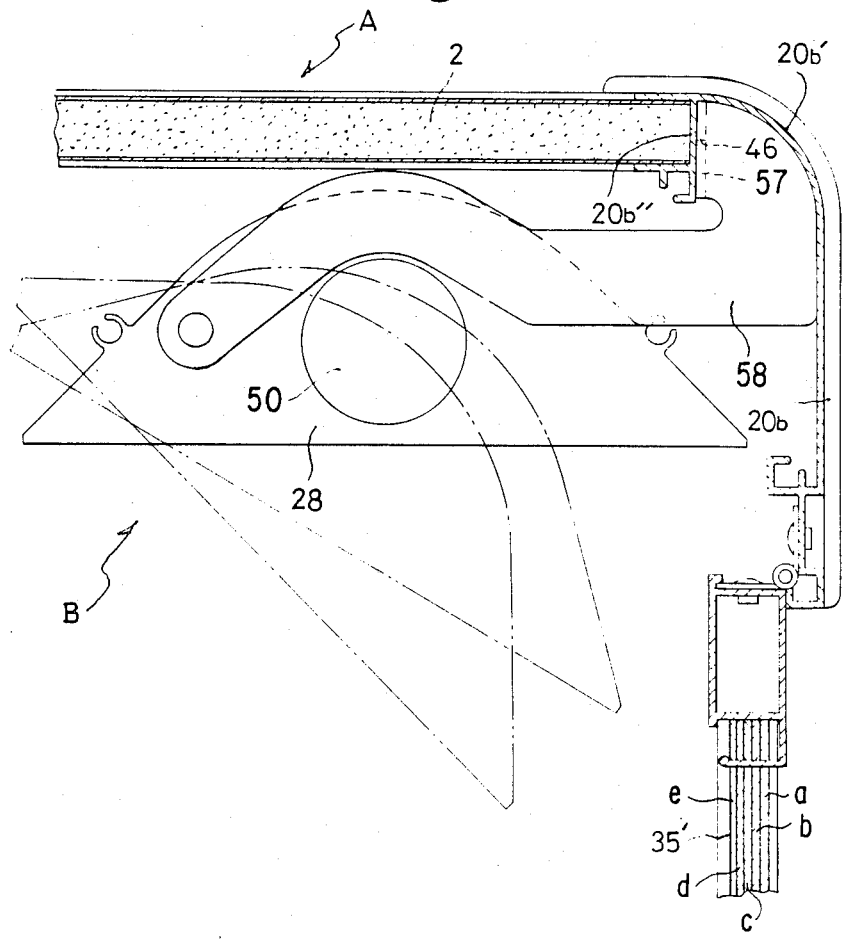

4,773,105

COLLAPSIBLE SAUNA BOX

FIELD OF THE INVENTION

This invention relates to a collapsible sauna box to be used as home far-infrared sauna in a private house, a ferroconcrete apartment house, an apartment house, etc.

DESCRIPTION OF THE PRIOR ART

As the prior art collapsible sauna box, to which the present invention appertains, Japanese Patent Publication No. 65163/1983 discloses one, which comprises a box body consisting of front and rear wall members constituted by respective reflecting panels and a heat-resistant foldable cover constituted by an aluminum-coated cloth or leather and serving as left and right side walls and a ceiling and far-infrared heaters provided on the inner surface of reflecting panels.

In this disclosed sauna box, the foldable cover serving as the left and right side walls and ceiling, as shown in FIG. 3 of the publication noted above, is a unified member to be folded in like a bellows along fine folding lines. Therefore, when the foldable cover is expanded, the left and right side walls and ceiling are not completely plane but are somewhat wavy due to elastic shrinkage tendency imparted to the cover with respect to the folding lines. For this reason, far-infrared rays are reflected randomly and do not efficiently irradiate the user.

Further, in the collapsed state of the collapsible sauna box the left and right side walls and ceiling are rather bulky due to the elastic shrinkage tendency of the foldable cover noted above.

If the folding lines are not provided, the foldable cover is not smoothly folded, and every time the cover is folded irregular folding lines are formed in the left and right side walls and ceiling. These irregular folding lines will remain as undesired wrinkles in the aluminum-coated cloth or leather.

In another aspect, in the disclosed collapsible sauna box the heaters are in the form of a thin box and secured to the inner surface of the front and rear wall members which are collapsibly united by the bellows-like heat-resistant foldable cover. This arrangement of the heaters, however, are unsatisfactory for the pertaining collapsible sauna box.

The collapsible sauna box of this type is designed to occupy a minimum installation space in use. By way of example, one which is disclosed as an example in the publication noted above has a width of 80 cm, a depth of 60 cm and a height of 120 cm in use. Where the heaters are secured to the front and rear wall members of such small sauna box, although the heaters are in the form of a thin box, they will still be obstructive and makes the interior of the expanded sauna box narrower, and the user in the sauna box will feel that he or she may strike the heaters when he or she respires and intends to lightly twist or move the upper body. Further, in view of uniform irradiation of the user with far-infrared rays, it is desired to arrange the heaters such that they face each other on the opposite side of the user. This arrangement of heaters, however, will sacrifice the compactness of the collapsible sauna box in the collapsed state. For this reason, it is inevitable to arrange the heaters such that they will not face each other.

Further, with the heaters provided in a face-to-face relation to each other on central portions of the inner surfaces of the front and rear walls and since the front and rear walls are constituted by respective sole panels, the folded left and right side walls and ceiling constituted by the foldable cover are not completely confined and concealed between the front and rear walls but partly outwardly extend therefrom because their thickness is not less than double the thickness of the mounted heaters.

SUMMARY OF THE INVENTION

An object of the invention is to provide a collapsible sauna box, in which left and right side and ceiling are constituted by respective distinct members with respective frames, and in its collapsed state the left and right wall members and ceiling member are completely confined and concealed between the front and rear walls overlapped over each other so that it is flat and compact and can be conveniently carried or stored.

Another object of the invention is to provide a collapsible sauna box, which comprises heaters capable of angle adjustment which are suited for the collapsible sauna box, i.e., which can irradiate the user with far-infrared rays in a face-to-face relation to each other on the opposite sides of the user and nevertheless do not sacrifice the compactness of the collapsible sauna box in the collapsed state.

BRIEF DESCRIPTION OF THE DRAWINGS

FIGS. 1 to 3 are a front view, a plan view and a right side view, respectively, showing an embodiment of the collapsible sauna box according to the invention;

FIG. 4 is a view showing the same embodiment in a collapsed state;

FIG. 5 is an enlarged-scale centrally vertical-sectional view, partly broken away, showing front and rear wall members;

FIG. 6 is a fragmentary enlarged-scale front view showing hinged portions of front and rear halves of side wall members;

FIG. 7 is a sectional view taken along line VII—VII in FIG. 6;

FIG. 8 is a sectional view taken along line VIII—VIII in FIG. 6;

FIGS. 10, 11(a), 11(b), 12(a) and 12(b) are a plan view, and left side and front views, respectively, showing upper and lower brackets used for mounting the heater;

FIG. 13 is a plan view showing a different heater capable of angle adjustment installed inside the collapsible sauna box according to the invention;

FIGS. 14, 15(a), 15(b), 16(a) and 16(b) are a plan view and left side and front views, respectively, showing upper and lower brackets used for mounting the heater; and FIGS. 17 and 18 are plan views showing the movable heaters, respectively, mounted inside a collapsible sauna box.

DETAILED DESCRIPTION OF THE PREFERRED EMBODIMENTS

The collapsible sauna box according to the invention comprises a collapsible box body, which consists of front and rear wall members, inwardly foldable left and right side wall members and a ceiling member pivoted at one end, and heaters pivoted for angle adjustment to brackets which can be mounted inside the collapsible box body at corners thereof. When the collapsible sauna box is in a collapsed state, the side wall members, ceiling member and heaters are completely confined between the front and rear wall members overlapped over each other.

Figure 1:
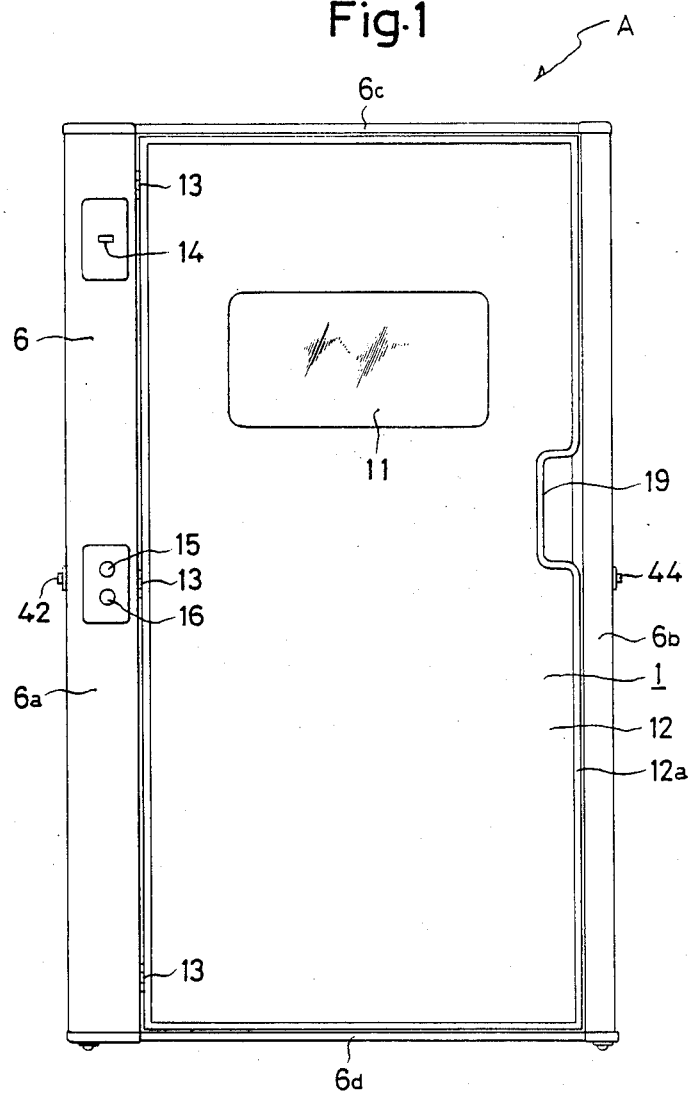
Figure 9:
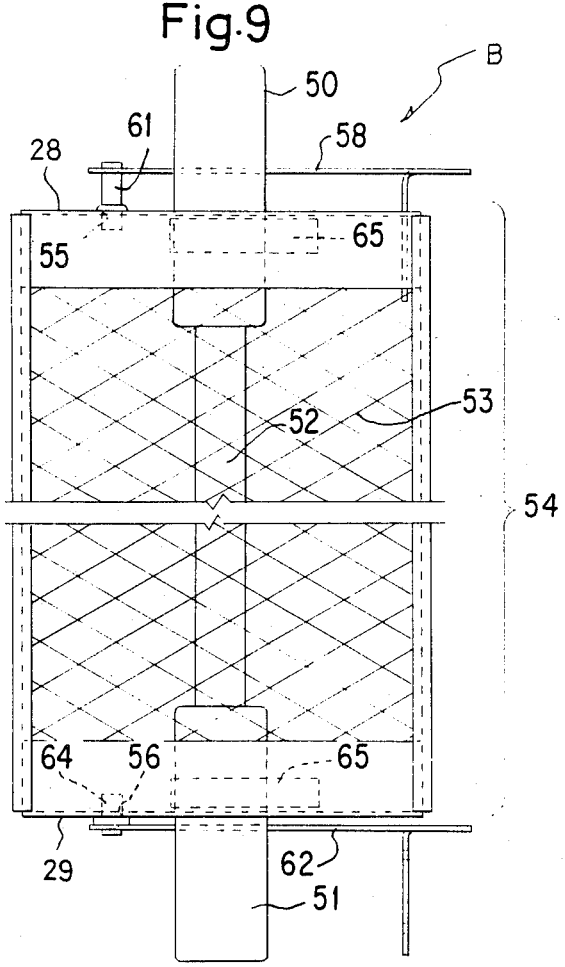
FIG. 9 is a front view showing a heater capable of angle adjustment installed inside the collapsible sauna box according to the invention.

Now, the invention will be described in conjunction with an embodiment thereof with reference to FIGS. 1 to 3 illustrating a basic mode of the invention.

Referring to the Figure, there is shown a collapsible sauna box A according to the invention, which comprises a collapsible box body consisting of front and rear wall members 1 and 2, inwardly foldable left and right side wall members 3 and 4 and a ceiling member 5 pivoted at one end. The wall members 1 to 4 and ceiling member 5 all have aluminum frames 6 to 10 which are light in weight. When the collapsible sauna box A is in a collapsed state, the left and right side wall members 3 and 4 and ceiling member 5 are completely confined between the front and rear wall members 1 and 2 overlapped over each other.

As shown in FIGS. 1 and 5, the front wall member 1 has a frame 6, which consists of left and right side frames 6a and 6b and upper and lower frames 6c and 6d. A door 12 having a window 11 is hinged by hinges 13 to the frame 6 such that it can occupy a front inner space of the frame 6. A power switch 14, a timer switch 15 and a power pilot lamp 16 are installed on the front surface of the left side frame 6a of the frame 6. The door 12 has an aluminum frame 12a and a urethane-filled panel 18 mounted therein. Aluminum foils 17 are applied to the opposite sides of the panel 18. If necessary, vinyl cloth (not shown) may be applied to the aluminum foils 17. Reference numeral 19 designates a cutting notch serving as a grip. The window 11 consists of an acrile plate.

As shown in FIG. 5, the rear wall member 2 has a frame 7, which consists of left and right side frames 20a and 20b and upper and lower frames 20c and 20d, and a urethane-filled panel 22 mounted in a rear portion of the frame 7. Aluminum foils 21 are applied to the opposite sides of the panel 22. If necessary, vinyl cloth may be applied to the aluminum foils 21.

As shown in FIG. 5, the ceiling member 5 has a frame 10 and a urethane-filled panel 24 mounted in the frame 10. Aluminum foils 23 are applied to the opposite sides of the panel 24. A cloth may be applied to the outer aluminum foil 23. Also if necessary, a vinyl cloth may be applied to the inner aluminum foil 23. A front end portion of the ceiling member 5 is hinged by a hinge 25 to the underside of the upper frame 6c of the front wall member 1. The ceiling member 5 has a magnet 27 secured to a rear end portion. The magnet 27 co-operates with a steel lock member 26 secured to the underside of the upper frame 20c of the rear wall member 2. The lock member 26 and magnet 27 constitute a door switch for far-infrared heaters B and C.

Reference numeral 30 designates a caster, and numeral 31 a leg member capable of height adjustment.

As shown in FIGS. 2, 6 and 7, the left and right wall members 3 and 4 consist of respective front halves 32 and 33 and rear halves 34 and 35. Frames 32a and 33a of the front halves 32 and 33 have their front end hinged by hinges 36 (shown in FIG. 3) to inner rear portions of the left and right frames 6a and 6b of the front wall member I. Frames 34a and 35a of the rear halves 34 and 35 have their rear end hinged by hinges 37 (shown in FIG. 3) to inner front portions of the left and right frames 20a and 20b of the rear wall member 2. The front and rear halves 32 to 35 have respective frames 32a to 35a. Opposed portions 32a' and 34a', and also 33a' and 35a', of the frames 32a and 34a, and also 33a and 35a, are hinged together by hinges 38 at upper, middle and lower positions so that the front and rear halves 32 to 35 can be inwardly folded and overlapped over one another as shown by phantom lines in FIG. 7. The hinged portions of the opposed portions 32a' and 34a', and also 33a' and 35a', are formed with outer notches 32a'' and 34a'', and also 33a'' and 35a'', at upper and lower positions. Pins 39 and 40 are secured to the inner hinged portions 32a' and 34a', and also 33a' and 35a, on the opposite sides of the notches 32a'' and 34a'', and also 33a'' and 35a''. Tension coil springs 41 are provided between the front and rear halves 32 and 34, and also 33 and 35 with their opposite ends 41a and 41b attached to the pins 39 and 40. Thus, the front and rear halves 32, 33 and 34, 35 can be stably held selectively in an expanded state and a folded state.

The halves 32 to 35 have respective heatresisting sheets 32' to 35' mounted in the frames 32a to 35a. The heat-resisting sheets 32' to 35' each are a lamination consisting from the outer side of a vinyl sheet a, a polyester sheet b, an aluminum foil c deposited on the polyester sheet b, a nylon sheet d and a vinyl chloride sheet e to decrease the weight for carrying easily by a hand like a woman and a child the folded and bottomless sauna box A.

Far-infrared heaters C and B are provided diagonally and for angle adjustment in central portions of the left and right frames 6a and 20b of the frames 6 and 7 of the front and rear wall members 1 and 2. In use, their angles are adjusted such that they face each other.

If desired, the exposed metal surfaces of the inner wall of the collapsible sauna box A may be given a hair embedding treatment.

Figure 10:
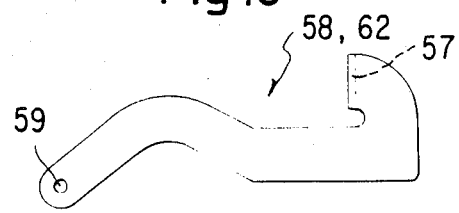

As shown in FIGS. 9 to 12, the heater B includes substantially semi-circular top and bottom plates 28 and 29, heater supports 50 and 51 mounted in the plates 28 and 29 such as to project substantially by one-half outwardly, i.e., upwardly and downwardly, a heater member 52 supported between the opposed inner surfaces of the supports 50 and 51 and a net 53 provided on the front side of the heater member 52. The overall semi-circular heater structure is designated at 54. The upper surface of the top plate 28 and the lower surface of the bottom plate 29 are formed with respective holes 55 and 56. The heater B also includes upper and lower brackets 58 and 62. FIGS. 10, 11(a), 11(b), 12(a) and 12(b) show the upper and lower brackets 58, 62. These brackets 58 and 62 each have a shape as shown in FIG. 10, with a hook-like end 57, which is secured to the inner wall of the collapsible sauna box A. They also each have a V-shaped portion, the free end of which, i.e., the end other than the hook-like end 57, is formed with a see-through hole 59. An upper pin 61 is secured to the upper bracket 58 by inserting its upper portion through the hole 59 and caulking the inserted portion as shown at 60. The upper pin 61 is inserted and rotatably supported in the upper hole 55. A lower pin 64, having a reinforcement flange portion is secured to the lower bracket 62 by inserting its lower portion through the hole 59 and caulking the inserted portion as shown at 63. The lower pin 64 is inserted and rotatably supported in the lower hole 56.

Reference numeral 65 designates mounting members for mounting the heater member supports 50 and 51, and numeral 46 screw holes.

As shown in FIGS. 13 to 16, the other heater C includes V-shaped upper and lower brackets 47 and 48, as shown in FIG. 14, in lieu of the upper and lower brackets 58 and 62 of the heater B which are somewhat longer and each have the hook-like end and V-shaped portion. For the rest, the heater C has the same structure as the heater B, and like parts are designated by like reference numerals.

The collapsible sauna box A having the above construction is collapsed as follows. First, the magnet 27 of the ceiling member 5 is pulled apart against the magnetic force of attraction from the lock member 26, and the ceiling member 5 is turned down about the hinges 25 to be accommodated in the frame 6 of the front wall member 1. Then, the front and rear halves 32 and 34, and also 33 and 35, of the left and right side wall members 3 and 4 are inwardly folded together against the tensile coil springs 41. As the front and rear halves 32 to 35 are folded, the front and rear wall members 1 and 2 approach each other and eventually overlap each other, so that the left and right side wall members 3 and 4 are confined and concealed between the front and rear wall members 1 and 2, as shown in FIG. 4. Afterwards, the male and female lock members 42 and 43, and also 44 and 45, are locked together.

For use, collapsible sauna box A is expanded by reversing the collapsing operation. More specifically, the male and female lock members 42 and 43, and also 44 and 45, are released, and then the front and rear wall members 1 and 2 are gradually pulled apart. At this time, the front and rear halves 32 and 34, and also 33 and 35, of the left and right side wall members 3 and 4 are expanded against the tensile coil springs 41 and are eventually brought to the fully expanded, i.e., straight, state. They are stably held in this state by the tensile coil springs 41. Thereafter, the ceiling member 5 is turned about the hinges 25 to a horizontal state. When it is turned to the horizontal state, it is locked in this state with the magnet 27 attracted to the lock member 26

Afterwards, a plug of a power code connected to the collapsible sauna box A is inserted into a receptable of a commercial power source connector (not shown), then a mat or the like is laid on the floor confined by the box A, and then the timer switch 15 is turned on. As a result, the pilot lamp 16 is lighted up, and far-infrared rays at about 50° C. are emitted from the far-infrared heaters B and C. Thus, the interior of the box A is filled with reflected rays from the aluminum foils 17, 21 and 23 of the front and rear wall members 1 and 2, left and right side wall members 3 and 4 and ceiling member 5. The user then enters the box A by opening the door 12 and is bathed in far-infrared rays for a preset period of time, e.g., 20 to 30 minutes, set by the timer switch 15. Far-infrared rays are absorbed in the skin and to cause resonant absorption phenomenon in the skin so that they reach the inner body. In consequence, not only sweat glands but also sebaceous glands are sufficiently opened so that the user gets clammy with respiration containing heavy metals such as lead and cadmium. The user thus can obtain sufficient sauna effects.

Figure 18:
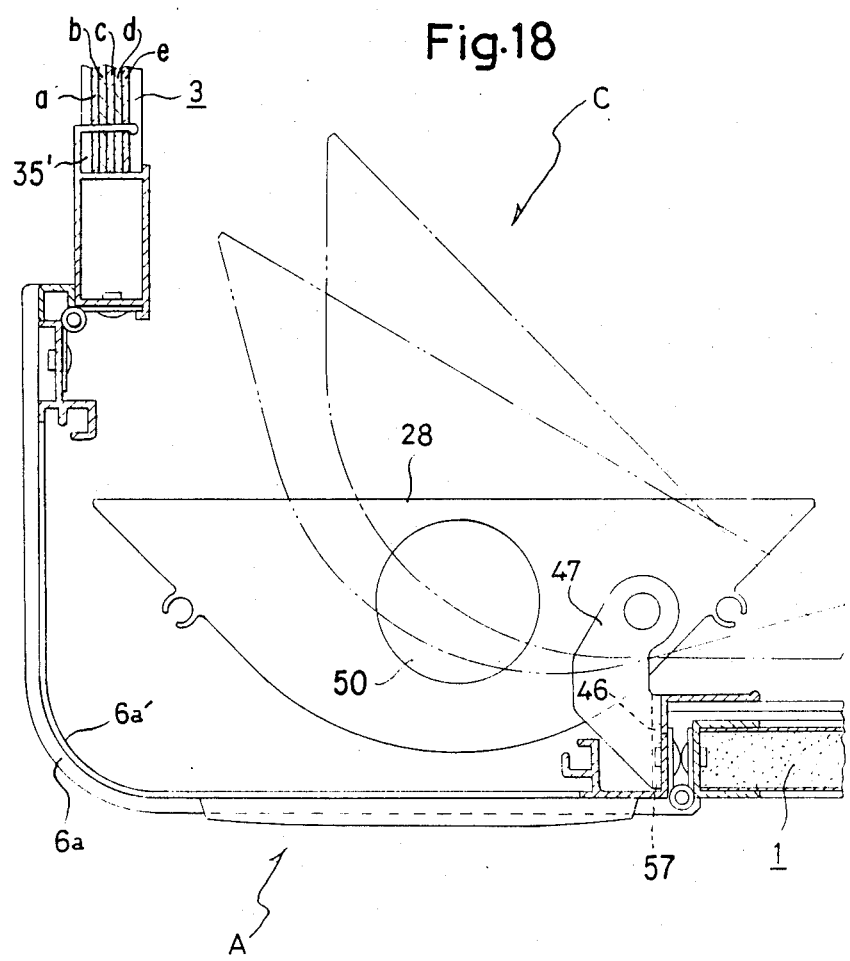

As shown in FIG. 17, the heater B may be mounted by securing the hook-like ends 57 of the upper and lower brackets 58 and 42 in an aligned state and using set screw (not shown) to an end of a receiving portion 20b″, which is provided at one end of a corner frame 20b′ of the rear wall member 2 of the collapsible sauna box A. As shown in FIG. 18, the heater C may be mounted by securing the hook-like ends 57 of the upper and lower brackets 47 and 48 in an aligned state and using set screws (not shown) to the inner side of a bent end of a corner frame 6a′ of the front wall member 1, to which the door hinges 13 are secured. In any of the heaters C and B, the heater structure 54 is capable of horizontal angle adjustment.

When using the collapsible sauna box A as shown in FIG. 2, the angles of the heaters 54 may be adjusted such that the heaters 54 are directed to the user $\alpha$ in the box A. Since the heaters 54 can be adjusted such that they face each other on the diagonally opposite sides of the user $\alpha$, the user $\alpha$ can receive uniform far-infrared rays. Further, since the heaters are installed in dead space, i.e., at corners, they are not obstructive. When collapsing the collapsible sauna box A, the heaters 54 are adjusted such that their front surface is parallel to the front or rear wall member 1 or 2. By so doing, the heater is completely accommodated in the corner frame 6a′ or 20b′ and is not obstructive when the collapsible sauna box A is in the collapsed state, as shown in FIG. 4.

With the collapsible sauna box according to the invention, all the components are made of material which is light in weight. As an example, the collapsible sauna box according to the invention may be as heavy as only 15 kg compared to 60 kg of the weight of the conventional non-collapsible wooden sauna box. Further, in the collapsed state, the collapsible sauna box according to the invention is flat and compact, and its occasional expansion is prevented by the male and female locking members 42 to 45. Thus, it can be conveniently transported and stored. It can be easily carried and handled by any person elder than a middle school boy or girl. Further, since it can be stored in the collapsed state, it can be used even in a comparatively narrow room of a ferroconcrete apartment house or the like.

In the case of the ordinary 100° C. steam sauna, in which one can continuously stay only 10 minutes at the most, the repeating of alternate sweating in the sauna and bathing in a water bath cause reduction of water content in the blood, so that one gets into hydrohydremia to feel fatigued and thirsty. With the collapsible sauna box according to the invention the user receives far-infrared rays at 40° to 50° C. Therefore, one will not feel thirsty even when he or she continuously stays in the box for 20 to 30 minutes. In addition, since there is no need of taking a water bath, no sudden physical condition changes occur. Further, since all the inner wall surfaces of the collapsible sauna box A are constituted by aluminum foils as reflectors, there is no possibility of leakage of far-infrared rays to the outside, and the collapsible sauna box according to the invention is very safe. Besides, there is provided a door switch mechanism, which causes the power source current to flow when and only when the magnet 27 is brought into contact with the lock member 26 with the expansion of the ceiling member 5 to the horizontal state. Thus, the far-infrared heaters are never occasionally operated when the collapsible sauna box 5 is in the collapsed state or when the ceiling member 5 is in the folded state.

Further, since the heaters are mounted at corners of the interior of the collapsible sauna box, they are not obstructive. Further, since the heaters are capable of angle adjustment, the user can receive far-infrared rays from the heaters facing each other on the opposite sides of the user. Further, the heaters will never deteriorate the compactness of the collapsible sauna box in the collapsed state. The collapsible sauna box according to the invention is thus very useful and beneficial in practice.

What is claimed is:

1. A collapsible sauna box, comprising a collapsible box body consisting of front and rear wall members, inwardly foldable left and right side wall members and a ceiling member pivoted at one end, and heaters pivoted for angle adjustments to brackets capable of being mounted inside said collapsible box body at corners thereof, said side wall members, ceiling member and heaters being completely confined between said front and rear wall members overlapped over each other when said collapsible box body is in a collapsed state, said brackets each having a hook-like end secured to the inner wall of said collapsible sauna box and a V-shaped portion formed adjacent to an end thereof with a see-through hole, a pin being fitted in said see-through hole and secured to said bracket, said pin being received in a hole formed in a top or bottom plate of said heaters.

2. A collapsible sauna box, comprising a collapsible box body consisting of front and rear wall members, inwardly foldable left and right side wall members and a ceiling member pivoted at one end, and heaters pivoted for angle adjustment to brackets capable of being mounted inside said collapsible box body at corners thereof, said side wall members, ceiling member and heaters being completely confined between said front and rear wall members overlapped over each other when said collapsible box body is in a collapsed state, said brackets each having a hook-like end secured to the inner wall of said collapsible sauna box and is formed adjacent to the other end with a see-through hole, a pin being fitted in said see-through hole and secured to said bracket, said pin being received in a hole formed in a top or bottom plate of said heaters.

3. A collapsible sauna box comprising front and rear wall means defining a front and rear wall, inwardly foldable left and right side walls pivotably mounted on said front and rear walls, a ceiling member pivotably mounted on said front and rear walls means, heater brackets mounted on one of said walls at opposite internal diagonal corners of said sauna box, each of said brackets having one end portion formed with a hook-like configuration secured to said one wall of the sauna box and another end portion having a see-through hole, a pin fitted in said see-through hole and secured to said bracket, infrared heater means pivotably mounted on each of said brackets for directing infrared rays to various locations within the interior of the sauna box, said heater means having a plate having a hole, said pin being received in said hole, switch means for controlling said heater means, said sauna box being collapsible from a non-collapsed state to a collapsed state as said foldable left and right side walls fold inwardly and said ceiling member is pivoted downwardly such that the folded left and right side walls, the downwardly pivoted ceiling member and said heater means are disposed between said front and rear walls, said switch means comprising one switch part on said ceiling member and another switch part on said front and rear wall means such that when said sauna box is in said non-collapsed state, said one switch part and said another switch part are in contact with one another, and when said sauna box is in said collapsed state, said one switch part and said another switch part are out of contact with one another.

4. A collapsible sauna box comprising front and rear wall means defining a front and rear wall, inwardly foldable left and right side walls pivotably mounted on said front and rear walls, a ceiling member pivotably mounted on said front and rear wall means, heater brackets mounted on one of said walls at opposite internal diagonal corners of said sauna box, each of said brackets having one end portion formed with a hook-like configuration secured to said one wall of said sauna box and another end portion formed with a V-shaped configuration and having a see-through hole, a pin fitted in said see-through hole and secured to said bracket, infrared heater means pivotably mounted on each of said brackets for directing infrared rays to various locations within the interior of the sauna box, said heater means having a plate having a hole, said pin being received in said hole, switch means for controlling said heater means, said sauna box being collapsible from a non-collapsed state to a collapsed state as said foldable left and right side walls fold inwardly and said ceiling member is pivoted downwardly such that the folded left and right side walls, the downwardly pivoted ceiling member and said heater means are disposed between said front and rear walls, said switch means comprising one switch part on said ceiling member and another switch part on said front and rear wall means such that when said sauna box is in said non-collapsed state, said one switch part and said another switch part are in contact with one another, and when said sauna box is in said collapsed state, said one switch part and said another switch part are out of contact with one another.

5. A collapsible sauna box according to claim 4 wherein said ceiling member is pivotably mounted on said front wall and said other switch part is mounted on said rear wall.

6. A collapsible sauna box according to claim 4, wherein said foldable left and right walls each comprise a front and rear half, each of said halves comprising a frame and a heat-resistant sheet means stretched on said frame, said heat-resistant sheet means being a lamination comprising a vinyl sheet, a polyester sheet, a nylon sheet and a vinyl chloride sheet, said sheet means decreasing the weight for hand carrying of the collapsed sauna box.

7. A collapsible sauna box according to claim 4, wherein said rear wall and said ceiling member each comprise a frame and a urethane-filled panel mounted in said frame, and an aluminum foil and a vinyl cloth on said urethane-filled panel to decrease the weight for hand carrying of the collapsed sauna box.

8. A collapsible sauna box according to claim 4, wherein said heaters have a semi-cylindrical outer shape.

* * * * *